(12) United States Patent
Yoshida (10) Patent No.: US 9,335,212 B2
(45) Date of Patent: May 10, 2016

(54) METHOD OF EVALUATING DISPERSION DEGREES OF MIXED EPOXY RESINS

(71) Applicant: HONDA MOTOR CO., LTD., Tokyo (JP)

(72) Inventor: Shuichiro Yoshida, Wako (JP)

(73) Assignee: HONDA MOTOR CO., LTD., Tokyo (JP)

(*) Notice: Subject to any disclaimer, the term of this patent is extended or adjusted under 35 U.S.C. 154(b) by 20 days.

(21) Appl. No.: 14/093,672

(22) Filed: Dec. 2, 2013

(65) Prior Publication Data

US 2014/0152984 A1 Jun. 5, 2014

(30) Foreign Application Priority Data

Dec. 4, 2012 (JP) ................. 2012-265021
Oct. 10, 2013 (JP) ................. 2013-212695

(51) Int. Cl.
*G01P 3/36* (2006.01)
*G01J 3/42* (2006.01)
*C08L 63/00* (2006.01)

(52) U.S. Cl.
CPC ... *G01J 3/42* (2013.01); *C08L 63/00* (2013.01)

(58) Field of Classification Search
CPC ........... G01J 3/42; C08L 63/02; G01N 21/27; G06F 19/10
See application file for complete search history.

(56) References Cited

U.S. PATENT DOCUMENTS 5,142,151 A 8/1992 Varnell et al.
7,435,600 B2 10/2008 Packard 2004/0099806 A1 5/2004 Shelley et al.
2011/0009528 A1* 1/2011 Tomioka et al. ............... 523/428
2013/0289887 A1* 10/2013 Huber .................... G01N 24/08
702/19

FOREIGN PATENT DOCUMENTS

| DE | 69017719 T2 | 9/1995 |
| JP | 2007-248431 | 9/2007 |
| JP | 2010-197099 | 9/2010 |
| JP | 2010197099 A * | 9/2010 |
| WO | 2004/048946 A1 | 6/2004 |
| WO | 2009/107697 | 9/2009 |

OTHER PUBLICATIONS

German Search Report dated Feb. 13, 2014, 10 pages.

* cited by examiner

*Primary Examiner* — Tarifur Chowdhury
*Assistant Examiner* — Jamil Ahmed
(74) *Attorney, Agent, or Firm* — Rankin, Hill & Clark LLP (57) ABSTRACT

A method of evaluating dispersion degrees of mixed epoxy resins includes, first, obtaining a resin mixture by mixing a plurality of aromatic epoxy resins, and taking a plurality of measurement samples from a plurality of sites of the resin mixture. The measurement samples are spectroscopically analyzed to obtain the spectra, and a plurality of common functional group peaks in the spectra are selected. The absorbances of the selected peaks are standardized to obtain absorbance ratios, based on the absorbance of a standard peak, in each of the spectra. Then, the standard deviations of the absorbance ratios of the selected peaks are calculated between the measurement samples. The maximum value of the obtained standard deviations is compared with a predetermined threshold value to evaluate the dispersion degrees of the aromatic epoxy resins.

7 Claims, 9 Drawing Sheets

| RESIN MIXTURE | [phr] | | | | | BIS(4-AMINOPHENYL) SULFONE | THRESHOLD VALUE |
|---|---|---|---|---|---|---|---|
| | MY 721 | jER 630 | jER 828 | jER 1001 | jER 1004AF | | |
| 1 | 30 | – | 10 | 30 | 30 | 26 | 0.11 |
| 2 | 30 | – | 30 | 10 | 30 | 30 | 0.04 |
| 3 | 30 | 40 | – | 30 | – | 47 | 0.02 |
| 4 | 30 | 50 | – | – | 20 | 51 | 0.02 |
| 5 | 30 | 50 | – | 20 | – | 52 | 0.02 |
| 6 | 30 | 50 | 20 | – | – | 56 | 0.02 |
| 7 | 49 | – | 21 | – | 30 | 36 | 0.08 |
| 8 | 50 | 23 | 13.5 | 13.5 | – | 42 | 0.04 |
| 9 | 50 | 50 | – | – | – | 60 | 0.03 |
| 10 | 52 | – | – | 30 | 18 | 34 | 0.02 |

FIG. 1

| RESIN MIXTURE | [phr] | | | | | | THRESHOLD VALUE |
|---|---|---|---|---|---|---|---|
| | MY 721 | jER 630 | jER 828 | jER 1001 | jER 1004AF | BIS(4-AMINOPHENYL) SULFONE | |
| 1 | 30 | – | 10 | 30 | 30 | 26 | 0.11 |
| 2 | 30 | – | 30 | 10 | 30 | 30 | 0.04 |
| 3 | 30 | 40 | – | 30 | – | 47 | 0.02 |
| 4 | 30 | 50 | – | – | 20 | 51 | 0.02 |
| 5 | 30 | 50 | – | 20 | – | 52 | 0.02 |
| 6 | 30 | 50 | 20 | – | – | 56 | 0.02 |
| 7 | 49 | – | 21 | – | 30 | 36 | 0.08 |
| 8 | 50 | 23 | 13.5 | 13.5 | – | 42 | 0.04 |
| 9 | 50 | 50 | – | – | – | 60 | 0.03 |
| 10 | 52 | – | – | 30 | 18 | 34 | 0.02 |

| MEASUREMENT / EVALUATION SUBJECT SAMPLE | p-DISUBSTITUTED BENZENE (1610cm⁻¹) | p-DISUBSTITUTED BENZENE (1593cm⁻¹) | p-DISUBSTITUTED BENZENE (1504cm⁻¹) | AROMATIC TERTIARY AMINE (1288cm⁻¹) | SULFONE GROUP (1103cm⁻¹) | EPOXY GROUP (904cm⁻¹) | p-DISUBSTITUTED BENZENE (826cm⁻¹) | p-DISUBSTITUTED BENZENE (548cm⁻¹) |
|---|---|---|---|---|---|---|---|---|
| S1 | 0.22 | 0.41 | 0.42 | 0.23 | 0.47 | 0.11 | 0.44 | 0.52 |
| S2 | 0.22 | 0.41 | 0.42 | 0.23 | 0.47 | 0.11 | 0.44 | 0.52 |
| S3 | 0.21 | 0.40 | 0.41 | 0.22 | 0.45 | 0.11 | 0.42 | 0.50 |
| S4 | 0.21 | 0.39 | 0.40 | 0.22 | 0.45 | 0.11 | 0.42 | 0.50 |
| S5 | 0.21 | 0.40 | 0.41 | 0.23 | 0.46 | 0.11 | 0.43 | 0.51 |
| S6 | 0.22 | 0.41 | 0.42 | 0.24 | 0.47 | 0.12 | 0.44 | 0.52 |
| S7 | 0.20 | 0.38 | 0.40 | 0.22 | 0.43 | 0.11 | 0.41 | 0.47 |
| S8 | 0.19 | 0.39 | 0.40 | 0.21 | 0.44 | 0.09 | 0.42 | 0.50 |
| S9 | 0.21 | 0.39 | 0.40 | 0.22 | 0.44 | 0.11 | 0.42 | 0.49 |
| S10 | 0.19 | 0.38 | 0.39 | 0.20 | 0.44 | 0.09 | 0.42 | 0.50 |

FIG. 7

| EVALUATION SUBJECT MEASUREMENT SAMPLE | p-DISUBSTITUTED BENZENE (1610cm$^{-1}$) | p-DISUBSTITUTED BENZENE (1593cm$^{-1}$) | p-DISUBSTITUTED BENZENE (1504cm$^{-1}$) | AROMATIC TERTIARY AMINE (1288cm$^{-1}$) | SULFONE GROUP (1103cm$^{-1}$) | EPOXY GROUP (904cm$^{-1}$) | p-DISUBSTITUTED BENZENE (826cm$^{-1}$) | p-DISUBSTITUTED BENZENE (548cm$^{-1}$) |
|---|---|---|---|---|---|---|---|---|
| S1 | 0.54 | 1.00 | 1.02 | 0.56 | 1.15 | 0.27 | 1.07 | 1.27 |
| S2 | 0.54 | 1.00 | 1.02 | 0.56 | 1.15 | 0.27 | 1.07 | 1.27 |
| S3 | 0.53 | 1.00 | 1.03 | 0.55 | 1.13 | 0.28 | 1.05 | 1.25 |
| S4 | 0.54 | 1.00 | 1.03 | 0.56 | 1.15 | 0.28 | 1.08 | 1.28 |
| S5 | 0.53 | 1.00 | 1.03 | 0.58 | 1.15 | 0.28 | 1.08 | 1.28 |
| S6 | 0.54 | 1.00 | 1.02 | 0.59 | 1.15 | 0.29 | 1.07 | 1.27 |
| S7 | 0.53 | 1.00 | 1.05 | 0.58 | 1.13 | 0.29 | 1.08 | 1.24 |
| S8 | 0.49 | 1.00 | 1.03 | 0.54 | 1.13 | 0.23 | 1.08 | 1.28 |
| S9 | 0.54 | 1.00 | 1.03 | 0.56 | 1.13 | 0.28 | 1.08 | 1.26 |
| S10 | 0.50 | 1.00 | 1.03 | 0.53 | 1.16 | 0.24 | 1.11 | 1.32 |
| STANDARD DEVIATION | 0.018 | — | 0.009 | 0.018 | 0.012 | 0.021 | 0.013 | 0.021 |

FIG. 8

| PEAK NUMBER | KNEADING TIME (MINUTE) WAVENUMBER (cm$^{-1}$) | STANDARD DEVIATION VALUE | | | | | |
|---|---|---|---|---|---|---|---|
| | | 0 | 1 | 3 | 5 | 10 | 30 |
| P1 | 1610 | 0.398 | 0.064 | 0.031 | 0.025 | 0.018 | 0.017 |
| P2 | 1504 | 0.593 | 0.222 | 0.075 | 0.027 | 0.009 | 0.008 |
| P3 | 1288 | 0.170 | 0.055 | 0.036 | 0.018 | 0.018 | 0.014 |
| P4 | 1103 | 0.078 | 0.044 | 0.042 | 0.017 | 0.012 | 0.022 |
| P5 | 904 | 0.313 | 0.039 | 0.045 | 0.026 | 0.021 | 0.023 |
| P6 | 826 | 0.502 | 0.246 | 0.080 | 0.026 | 0.013 | 0.008 |
| P7 | 548 | 0.162 | 0.066 | 0.049 | 0.013 | 0.021 | 0.060 |

FIG. 9

METHOD OF EVALUATING DISPERSION DEGREES OF MIXED EPOXY RESINS

CROSS-REFERENCE TO RELATED APPLICATIONS

This application is based upon and claims the benefit of priority from Japanese Patent Applications No. 2012-265021 filed on Dec. 4, 2012 and No. 2013-212695 filed on Oct. 10, 2013, the contents all of which are incorporated herein by reference.

BACKGROUND OF THE INVENTION

1. Field of the Invention

The present invention relates to a method of evaluating dispersion degrees of a plurality of aromatic epoxy resins in a resin mixture obtained by mixing the aromatic epoxy resins.

2. Description of the Related Art

Lightweight, high-strength, fiber-reinforced plastics have been widely used in various fields. For example, in the case of using the fiber-reinforced plastic in a member of an aircraft, the fiber-reinforced plastic is required to have excellent heat resistance, impact resistance, etc. It is difficult to prepare a matrix resin having excellent various properties from one epoxy resin. Therefore, a resin mixture is prepared as the matrix resin by mixing a plurality of epoxy resins in combination.

For example, as proposed in International Publication No. WO 2009/107697, a plurality of epoxy resins having different properties are mixed to prepare the resin mixture. This resin mixture exhibits notable properties different from those of each epoxy resin. The resin mixture, superior to a single epoxy resin, can be used as the matrix resin of the fiber-reinforced plastic for the aircraft member.

In a case where the resin mixture is not sufficiently mixed, the epoxy resins cannot be uniformly dispersed. When the resin mixture is poor in the dispersion of the mixed epoxy resins, the structural material containing the resin mixture exhibits non-uniform properties. For example, in a local position of the material, the physical and mechanical properties may be deteriorated, lowering the heat resistance, the mechanical strength, etc.

In addition, in a case where the epoxy resins are not sufficiently mixed with a hardener by kneading, the epoxy resins and the hardener cannot be uniformly dispersed. When the resin mixture is poor in the dispersion of the mixed epoxy resins, the structural material containing the hardened resin mixture exhibits non-uniform properties. For example, in a local position of the material, the physical and mechanical properties may be deteriorated, extremely lowering the heat resistance, the mechanical strength, etc.

Thus, in view of improving the properties of the structural material containing the resin mixture over the entire material, it is necessary to sufficiently disperse the epoxy resins (and the hardener) in the resin mixture. For example, the sufficient dispersion can be achieved by mixing the components for a longer time under a greater stirring force. However, when the kneading is continued even after the epoxy resins (and the hardener) are sufficiently dispersed, the production efficiencies of the resin mixture and the fiber-reinforced plastic may be deteriorated, and unexpectedly the resin mixture may be excessively hardened.

For the above reasons, in view of dispersing the epoxy resins (and the hardener) efficiently and sufficiently without excess mixing time, there is a demand for a method of obtaining information of the dispersion degrees of the epoxy resins in the resin mixture, i.e. a method of evaluating the dispersion degrees of the epoxy resins (and the hardener).

In the past, the dispersion degrees of the mixed resins have generally been evaluated by visual observation. However, in the visual observation, the dispersion evaluation depends on the visual sense of the observer. Therefore, the dispersion degrees of the mixed resins are qualitatively evaluated, and cannot be quantitatively evaluated. Furthermore, for example, in a case where all the mixed epoxy resins are transparent and do not change the color of the resin mixture after the dispersion, it is difficult to evaluate the dispersion degrees of the mixed resins by the visual observation.

The dispersion degrees of the mixed resins can be quantitatively evaluated by analyzing a sea-island structure of the resin mixture using a transmission electron microscope (TEM). In fact, the dispersion degrees can be supposedly evaluated by using the TEM for observing the sea-island structure of the resin mixture and by calculating the area ratio between the sea epoxy resin and the island epoxy resin.

A use of a Fourier transform infrared spectroscopy (FT-IR) for an analysis of epoxy resins in a resin composition is proposed in Japanese Laid-Open Patent Publication No. 2010-197099. Specifically, in this method, the hardening degree of the resin composition is measured by detecting an infrared absorption peak of an aromatic epoxy resin contained in the resin composition. Epoxy groups in the aromatic epoxy resin are opened and reduced with progression of a hardening reaction. Meanwhile, the number of benzene rings in the aromatic epoxy resin is not changed in the hardening reaction. Thus, the progression of the hardening reaction of the resin composition can be evaluated by measuring temporal change of the ratio between the infrared absorption peaks of the epoxy groups and the benzene rings and by detecting the reduction of the epoxy groups.

SUMMARY OF THE INVENTION

In the method using the TEM in the sea-island structure analysis for evaluating the dispersion degrees of the mixed resins, it is necessary to prepare a measurement sample for the TEM observation and a vacuum sample chamber for the measurement sample. Thus, in this method, complicated operations are required for obtaining the observation results, and it is difficult to readily evaluate the dispersion degrees of the mixed resins. Furthermore, only an area, which can be observed by the TEM, is evaluated, and the dispersion of the entire kneaded resin mixture cannot be evaluated. In addition, in a case where the epoxy resins in the mixture have similar electron beam transmission properties, it is difficult to calculate the above-described area ratio using the TEM, thus to evaluate the dispersion degrees of the mixed epoxy resins. Furthermore, in a case where the hardener is added to the epoxy resins, the hardening reaction may proceed even in the observation operations depending on the environmental temperature, and it is more difficult to evaluate the dispersion degrees.

In the epoxy resin analysis method described in Japanese Laid-Open Patent Publication No. 2010-197099, the temporal structural changes of the epoxy resins by the hardening reaction is detected by the FT-IR. However, in the process of mixing and dispersing the epoxy resins, peaks corresponding to the epoxy groups are not greatly changed depending on the basic structures (main chains) of the molecules. Therefore, the structural changes of the epoxy resins by the dispersion are hardly observed. Thus, when the ratios between the infrared absorption peaks of the epoxy groups and the benzene rings are measured and compared before and after the kneading of the resin mixture, it is difficult to readily evaluate the dispersion degrees using the comparison result. Consequently, it is difficult to use the analysis method described in Japanese Laid-Open Patent Publication No. 2010-197099 for quantitatively and highly accurately evaluating the dispersion degrees.

Thus, in view of optimizing the mixing conditions for preparing the resin mixture and improving the properties of the structural material containing the resin mixture, there is a strong demand for the method of evaluating the dispersion degrees of the mixed epoxy resins. However, a method, which is capable of readily and quantitatively evaluating the dispersion degrees of the mixed epoxy resins regardless of the colors and the electron beam transmission properties of the resins, has not been proposed so far.

A principal object of the present invention is to provide a method capable of readily and quantitatively evaluating dispersion degrees of a plurality of aromatic epoxy resins in a resin mixture obtained by mixing the aromatic epoxy resins.

According to an aspect of the present invention, there is provided a method of evaluating dispersion degrees of a plurality of aromatic epoxy resins in a resin mixture obtained by mixing the aromatic epoxy resins, the method comprising the steps of: taking a plurality of measurement samples from a plurality of sites of the resin mixture, spectroscopically analyzing the measurement samples to obtain spectra, selecting a plurality of common functional group peaks in the spectra, standardizing absorbances of the selected peaks to obtain absorbance ratios, based on an absorbance of a standard peak, in each of the spectra, calculating standard deviations of the absorbance ratios of the selected peaks between the measurement samples, and comparing a maximum value of the standard deviations with a predetermined threshold value to evaluate the dispersion degrees of the aromatic epoxy resins.

In this method of evaluating the dispersion degrees of the epoxy resins in the resin mixture, the measurement samples are taken from the sites of the resin mixture and spectroscopically analyzed, respectively. The differences between the spectra of the measurement samples, depending on the positions in the resin mixture, are detected from the analysis results. When the epoxy resins have higher dispersion degrees and the resin mixture has a more uniform composition, the spectra exhibit smaller differences. Thus, the dispersion degrees of the mixed epoxy resins can be evaluated based on the detected differences between the spectra.

Specifically, a plurality of peaks corresponding to important functional groups in the aromatic epoxy resins are selected in the spectrum obtained by spectroscopically analyzing the measurement sample. The particular standard peak is further selected from the selected peaks. The standard peak is considered to have a height (absorbance) of 1, and the absorbances of the other selected peaks are standardized (normalized) based on the absorbance of the standard peak, whereby the absorbance ratios are obtained.

A plurality of common functional group peaks in a plurality of the measurement samples are selected, and the absorbance ratios of the selected peaks are obtained in each of the measurement samples in the same manner. Then, the standard deviation of the absorbance ratios of each selected peak is calculated between the measurement samples.

The differences between the absorbance ratios of each selected peak (i.e. the differences between the spectra), depending on the positions in the resin mixture, can be detected from the standard deviation.

Specifically, a resin mixture, which has sufficient epoxy resin dispersion degrees and can exhibit sufficient properties in a structural material, is prepared, and the standard deviations of the resin mixture are obtained in the above manner, whereby the threshold value for evaluating the dispersion degree is obtained. For example, the maximum value of the standard deviations of the selected peaks may be used as the threshold value. Thus, the standard deviations of the subject (resin mixture) to be evaluated are calculated in the above manner, and the maximum value of the standard deviations is compared with the threshold value, whereby the dispersion degrees of the mixed epoxy resins can be quantitatively evaluated.

When the calculated standard deviations are equal to or smaller than the threshold value, the resin mixture can be considered to have sufficient epoxy resin dispersion degrees and to improve the properties of a structural material containing the resin mixture. On the other hand, when the calculated standard deviations are larger than the threshold value, the resin mixture can be considered to have an insufficient epoxy resin dispersion degree.

Consequently, in the method of the present invention, the dispersion degrees of the mixed epoxy resins can be quantitatively evaluated, regardless of the colors and the electron beam transmission properties of the resins, by the simple operations of spectroscopically analyzing the resin mixture, calculating the absorbance ratios and the standard deviations from the functional group peak absorbances, and comparing the maximum value of the standard deviations with the threshold value.

It takes only several minutes to perform the spectroscopic analysis. Therefore, as compared with the method using the TEM or the like, the method of the present invention is capable of more readily evaluating the dispersion degrees of the epoxy resins in a shorter time. Furthermore, the measurement samples are taken from a plurality of the sites of the resin mixture. Therefore, the area to be evaluated is not limited, and the dispersion degrees can be evaluated over the entire resin mixture.

The measurement samples are spectroscopically analyzed to obtain the spectra, a plurality of the peaks are selected in the spectra, and the standard deviations of the selected peaks are calculated respectively. Thus, the dispersion degrees of the mixed epoxy resins are evaluated based on a plurality of the standard deviations. Therefore, the dispersion degrees can be highly accurately evaluated. In view of increasing the dispersion degrees of the mixed epoxy resins (i.e. reducing the standard deviation values), highly accurate results can be obtained by evaluating the dispersion degrees based on the maximum value of the standard deviations.

The absorbances of the selected peaks are standardized based on the absorbance of the particular standard peak in each spectrum, and the standard deviations of thus-obtained absorbance ratios are calculated. Therefore, the evaluation results are hardly affected by a measurement error of a spectroscopic analyzer and can be highly accurately obtained.

Alternatively, an average value of the standard deviations of the selected peaks may be calculated to quantify the dispersion degrees of the epoxy resins. In this case, the dispersion degrees of the mixed epoxy resins can be represented by numerical values, and thereby can be quantitatively evaluated.

As described above, the method of the present invention is capable of readily and quantitatively evaluating the dispersion degrees of the aromatic epoxy resins in the resin mixture obtained by mixing the resins. Consequently, the method is capable of dispersing the epoxy resins in a minimal time under optimized mixing conditions and efficiently improving the properties of a structural material containing the resin mixture.

It is preferred that the resin mixture contains at least two of a polyfunctional glycidylamine-type epoxy resin represented by the following structural formula (1), a p-aminophenol-type liquid epoxy resin represented by the following structural formula (2), and a bisphenol A-type liquid epoxy resin or a bisphenol A-type solid epoxy resin represented by the following structural formula (3):

tural material can be prevented from having non-uniform properties. Thus, the property deterioration in a local position of the structural material can be prevented. For example, in the local position of the structural material, the deterioration of the physical and mechanical properties can be prevented, so that the reduction of the heat resistance, the mechanical strength, and the like can be prevented. Consequently, an wherein n is the number (i.e. the polymerization degree) of the repeating units in the structural formula (3). At room temperature, the bisphenol A-type epoxy resin is a liquid component when n is a small number, and the bisphenol A-type epoxy resin is a solid component when n is a large number.

It is preferred that the resin mixture is obtained by mixing 30 to 52 phr of the polyfunctional glycidylamine-type epoxy resin and 70 to 48 phr of at least one of the p-aminophenol-type liquid epoxy resin, the bisphenol A-type liquid epoxy resin, and the bisphenol A-type solid epoxy resin.

It is further preferred that the resin mixture is obtained by mixing 30 to 52 phr of the polyfunctional glycidylamine-type epoxy resin, 23 to 50 phr of the p-aminophenol-type liquid epoxy resin, 10 to 30 phr of the bisphenol A-type liquid epoxy resin, and 10 to 30 phr of the bisphenol A-type solid epoxy resin.

Such a resin mixture, which has appropriate composition ratios and sufficient dispersion degrees of the aromatic epoxy resins, can be efficiently obtained by using the method of the present invention for evaluating the dispersion degrees. The resin mixture can be used for preparing a structural material having excellent properties such as heat resistance and impact resistance. Thus, the resin mixture can be used in the structural material suitable for an aircraft member.

It is preferred that 26 to 60 parts by weight of a hardener is added to 100 parts by weight of the aromatic epoxy resins in the resin mixture. As described above, the dispersion degrees of the aromatic epoxy resins can be readily and quantitatively evaluated. Therefore, also the hardener can be sufficiently dispersed in the resin mixture as well as the epoxy resins. Consequently, the entire resin mixture can be appropriately and efficiently hardened to obtain the structural material having excellent properties such as the heat resistance and mechanical strength.

It is preferred that the threshold value is 0.01 to 0.11 in the evaluation of the dispersion degrees of the epoxy resins in the above resin mixture. By evaluating the dispersion degrees of the epoxy resins based on this threshold value, the dispersion degrees can be sufficiently increased in the resin mixture. Therefore, the properties of the structural material containing the resin mixture can be sufficiently improved, and the strucaircraft member having high durability, heat resistance, impact resistance, and reliability can be prepared from the resin mixture.

It is preferred that the measurement samples are spectroscopically analyzed by a Fourier transform infrared spectroscopy, and the absorbances of the selected peaks are standardized to obtain the absorbance ratios based on the absorbance of a benzene ring at 1593 $cm^{-1}$. The spectroscopic analysis using the Fourier transform infrared spectroscopy (FT-IR) is capable of obtaining more accurate results in a shorter time as compared with an analysis using a dispersion-type infrared spectroscopy or the like. Thus, by using the FT-IR, the dispersion degrees of the mixed epoxy resins can be highly accurately evaluated in a shorter time.

The benzene ring corresponding to the peak at 1593 $cm^{-1}$ is structurally stable, and the peak of the benzene ring is clearly shown in the spectra in many cases. Therefore, when the absorbance ratios are calculated based on the absorbance of the benzene ring, the dispersion degrees of the epoxy resins can be more accurately and readily evaluated.

The above and other objects, features and advantages of the present invention will become more apparent from the following description when taken in conjunction with the accompanying drawings in which a preferred embodiment of the present invention is shown by way of illustrative example.

DESCRIPTION OF THE PREFERRED EMBODIMENTS

An embodiment of the epoxy resin dispersion degree evaluation method of the present invention will be described in detail below with reference to the accompanying drawings. In this embodiment, resin mixtures having improved properties, suitable for use in a structural material for an aircraft member or the like, are evaluated by the method.

In this embodiment, each resin mixture contains aromatic epoxy resins and a hardener to be hereinafter described. The resin mixture used in the epoxy resin dispersion degree evaluation method of the present invention is not particularly limited thereto, and may be prepared by mixing a plurality of epoxy resins having different chemical structures or molecular weights. Furthermore, the hardener in the resin mixture is not particularly limited to the substance to be hereinafter described, and the resin mixture may contain no hardeners.

In this embodiment, the resin mixture to be evaluated with respect to the dispersion degrees is obtained by mixing at least two aromatic epoxy resins selected from a polyfunctional glycidylamine-type epoxy resin represented by the following structural formula (1), a p-aminophenol-type liquid epoxy resin represented by the following structural formula (2), and a bisphenol A-type liquid epoxy resin or a bisphenol A-type solid epoxy resin represented by the following structural formula (3). Bis(4-aminophenyl)sulfone is added as the hardener to the resin mixture.

cially available product such as jER630 (available from Mitsubishi Chemical Corporation) may be used.

Among the bisphenol A-type liquid and solid epoxy resins (polycondensation products of 4,4'-isopropylidenediphenol and 1-chloro-2,3-epoxypropane), as the bisphenol A-type liquid epoxy resin, a commercially available product such as jER828 (available from Mitsubishi Chemical Corporation) may be used. As the bisphenol A-type solid epoxy resin, a commercially available product such as jER1001 or jER1004AF (available from Mitsubishi Chemical Corporation) may be used. The liquid or solid state of the bisphenol A-type epoxy resin depends on the number n in the structural formula (3).

In the above description, Araldite and jER are registered trademarks.

In this embodiment, the resin mixture is used in the structural material (e.g. as a matrix resin of a fiber-reinforced plastic), and it is preferred that 30 to 52 phr of the polyfunctional glycidylamine-type epoxy resin and 70 to 48 phr of at least one of the p-aminophenol-type liquid epoxy resin, the bisphenol A-type liquid epoxy resin, and the bisphenol A-type solid epoxy resin are mixed. In this case, the structural material can be excellent in various properties such as heat resistance, durability, and strength. It is further preferred that 30 to 52 phr of the polyfunctional glycidylamine-type epoxy resin, 23 to 50 phr of the p-aminophenol-type liquid epoxy resin, 10 to 30 phr of the bisphenol A-type liquid epoxy resin, and 10 to 30 phr of the bisphenol A-type solid epoxy resin are mixed.

The term "phr (per hundred resin)" means the weight ratio of each aromatic epoxy resin to the total 100 of the aromatic epoxy resins in the resin mixture.

The amount of the hardener is preferably 26 to 60 parts by weight per 100 parts by weight of the aromatic epoxy resins.

The hardener may be selected from aromatic polyamines (such as bis(4-aminophenyl)sulfone, metaphenylenediamine, and diaminodiphenylmethane) and alicyclic polyamines (such as isophoronediamine and norbornenediamine), depending on the intended use in the aircraft member, etc. In this embodiment, bis(4-aminophenyl)sulfone is used as the hardener.

In the structural formula (3), n is the number of the repeating units.

As the polyfunctional glycidylamine-type epoxy resin (N,N,N',N'-tetrakis(oxiran-2-ylmethyl)-4,4'-methylenedianiline), a commercially available product such as Araldite MY721 (available from Huntsman Advanced Materials) may be used.

As the p-aminophenol-type liquid epoxy resin (N,N-bis(2, 3-epoxypropyl)-4-(2,3-epoxypropoxy)aniline), a commer- Calculation of threshold values for evaluating the dispersion degrees of the epoxy resins in the resin mixtures 1 to 10 will be described below. The resin mixtures 1 to 10 are prepared by mixing and kneading the above-described commercially available products and hardener at the ratios shown in FIG. 1, respectively. Incidentally, in the resin mixtures 1 to 10, the epoxy resins are sufficiently mixed and approximately uniformly dispersed.

Figure 2:
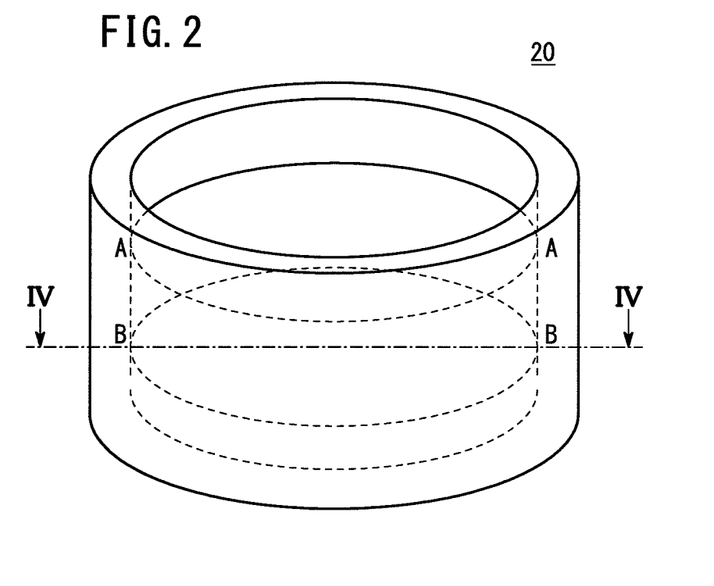
FIG. 2 is an overall, schematic, perspective view of a vessel used in a process of mixing the aromatic epoxy resins, which has sampling sites for collecting measurement samples from the resin mixture.
Figure 3:
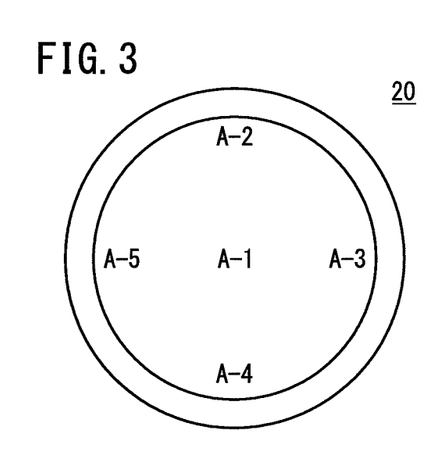
FIG. 3 is a detail top view of the sampling sites in the plane A of FIG. 2.
Figure 4:
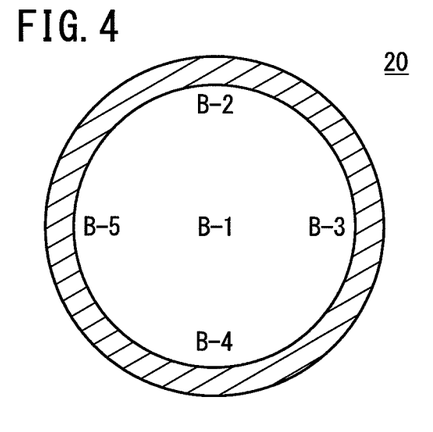
FIG. 4 is a detail cross-sectional view of the sampling sites in the plane B of FIG. 2, taken along the line IV-IV in the direction of the arrows.

An example of the resin mixture 10 will be described below. FIG. 2 is an overall, schematic, perspective view of a kneading vessel 20 containing the resin mixture 10, FIG. 3 is a top view of the kneading vessel 20, and FIG. 4 is a cross-sectional view taken along the line IV-IV in the direction of the arrows of FIG. 2. The resin mixture 10 is sufficiently mixed in the kneading vessel 20. Then, for example, ten sampling sites A1 to A5 and B1 to B5 are selected as shown in FIGS. 2 to 4.

Specifically, the sampling sites A1 to A5 shown in FIG. 3 are located in a plane at the height represented by the dashed line A in FIG. 2 (in the vicinity of the liquid surface of the resin mixture 10). Furthermore, the sampling sites B1 to B5 shown in FIG. 4 are located in a plane at the height represented by the dashed line B in FIG. 2 (2 to 3 mm away from the bottom of the kneading vessel 20). The sampling sites A1 and B1 are located in the same position at different depths as viewed from above. The sampling sites A2 and B2, A3 and B3, A4 and B4, and A5 and B5 have the same positional relation, respectively. A plurality of portions of the resin mixture 10 are taken as measurement samples S1 to S10 from the sampling sites A1 to A5 and B1 to B5. The amounts of the portions are such that the measurement samples S1 to S10 can be spectroscopically analyzed.

Then, thus-obtained measurement samples S1 to S10 are spectroscopically analyzed by an FT-IR, respectively. An attenuated total reflection (ATR) method may be used in the spectroscopic analysis.

Figure 5:
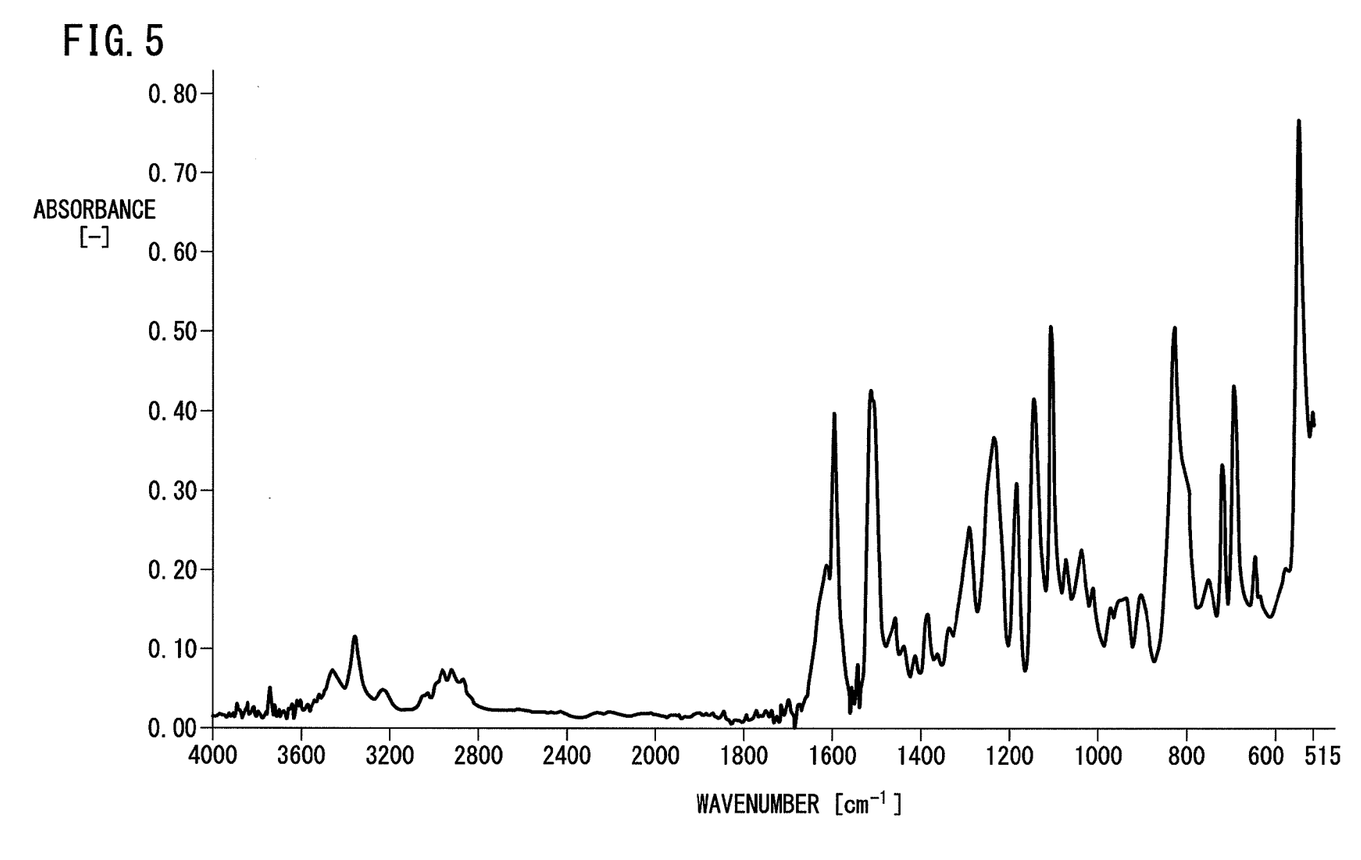
FIG. 5 is an example of spectra obtained by an FT-IR spectroscopic analysis of the measurement samples.

The measurement samples S1 to S10 are spectroscopically analyzed in this manner to obtain the infrared absorption spectra (which may be referred to simply as the spectra) of the sampling sites A1 to A5 and B1 to B5 in the resin mixture 10. The spectrum obtained by spectroscopically analyzing the measurement sample S1 is shown in FIG. 5. In FIG. 5, the wavenumber is on the horizontal axis, and the absorbance is on the vertical axis.

In the obtained spectrum, a plurality of peaks corresponding to major functional groups of the aromatic epoxy resins are selected. In this embodiment, eight peaks are selected in the spectrum of FIG. 5. The eight peaks include a peak at 1610 $cm^{-1}$ corresponding to a p-disubstituted benzene, a peak at 1593 $cm^{-1}$ corresponding to a p-disubstituted benzene, a peak at 1504 $cm^{-1}$ corresponding to a p-disubstituted benzene, a peak at 1288 $cm^{-1}$ corresponding to an aromatic tertiary amine, a peak at 1103 $cm^{-1}$ corresponding to a sulfone group, a peak at 904 $cm^{-1}$ corresponding to an epoxy group, a peak at 826 $cm^{-1}$ corresponding to a p-disubstituted benzene, and a peak at 548 $cm^{-1}$ corresponding to a p-disubstituted benzene.

Figure 6:
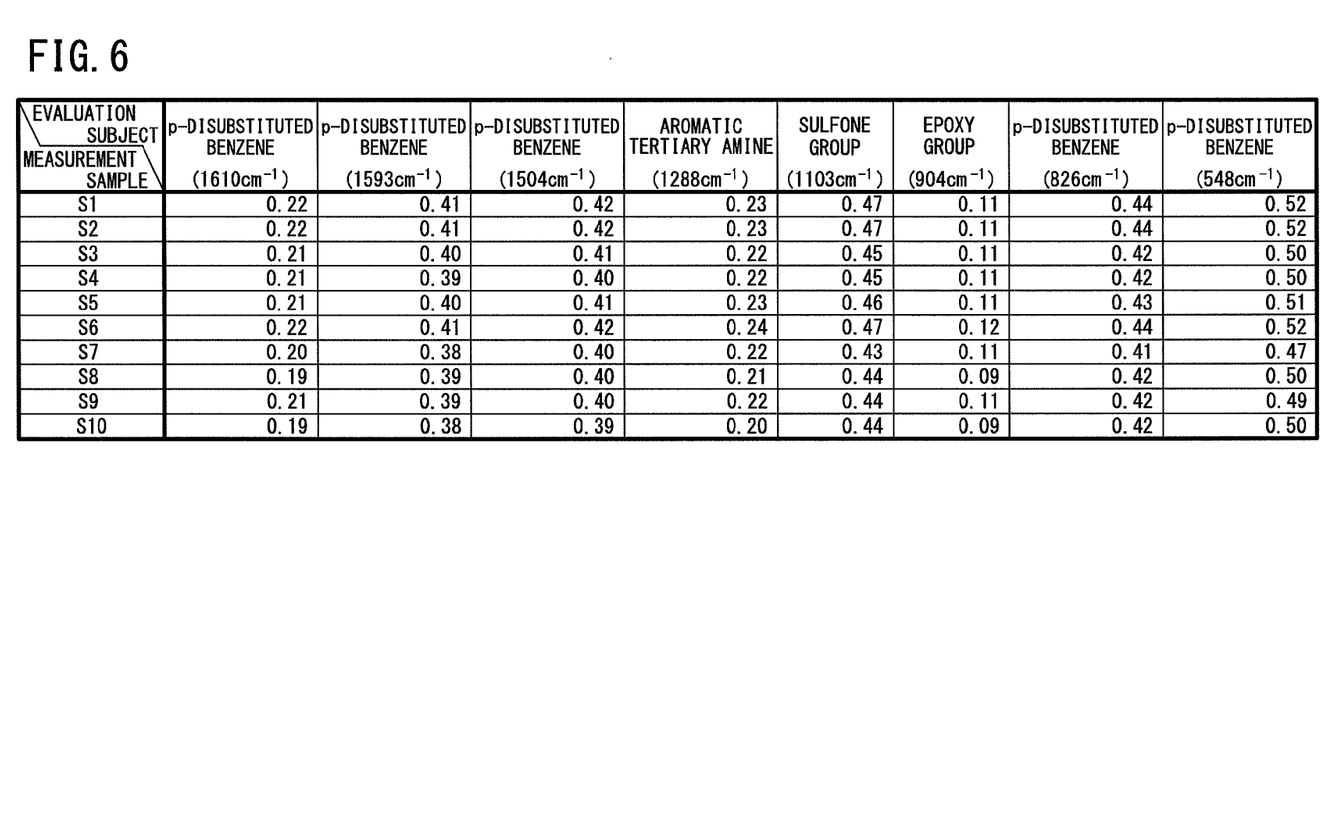
FIG. 6 is a table showing the absorbances of selected peaks of the measurement samples.

Also in the spectra of the other measurement samples S2 to S10, the peaks corresponding to the functional groups are selected in the same manner. Thus, a plurality of common functional group peaks of the measurement samples S1 to S10 are selected, and the heights of the selected peaks are measured, respectively. Then, as shown in FIG. 6, the absorbances of each selected peak of the measurement samples S1 to S10 are obtained.

In each of the measurement samples S1 to S10, the absorbances of the selected peaks are standardized, based on the absorbance of a standard peak at 1593 $cm^{-1}$ corresponding to the p-disubstituted benzene (the standard absorbance), to obtain the absorbance ratios. Thus, the absorbances of the selected peaks are divided by the standard absorbance, respectively, to calculate the absorbance ratios to the standard absorbance of 1.

Figure 7:
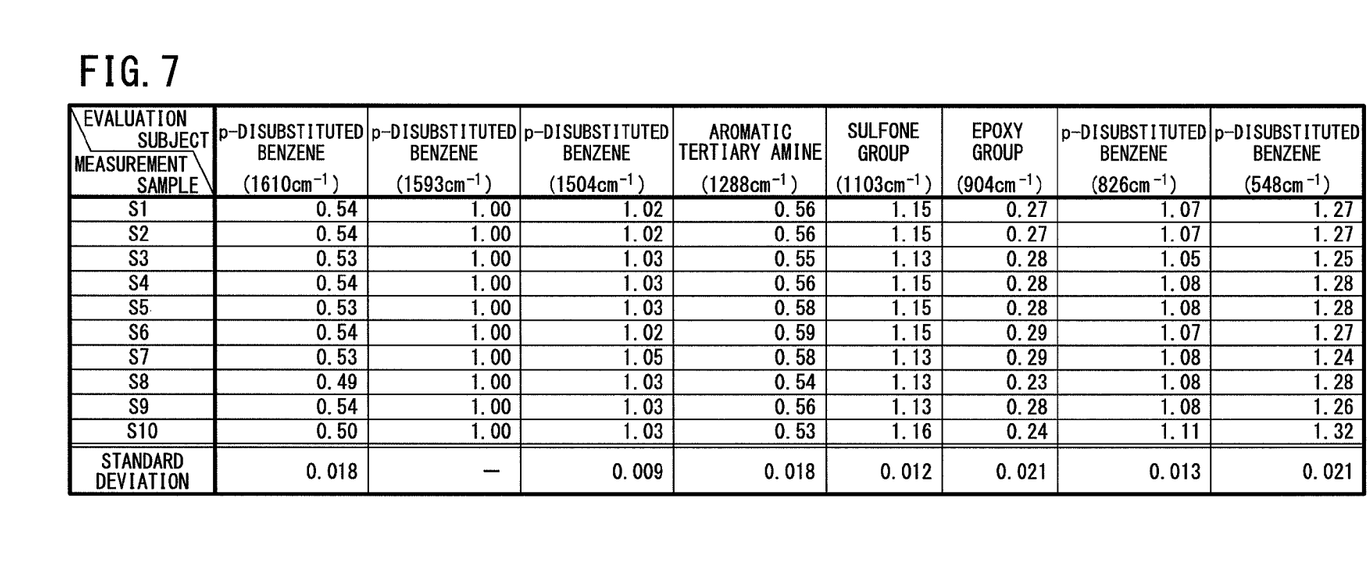
FIG. 7 is a table showing the absorbance ratios of the selected peaks of the measurement samples and standard deviations of the absorbance ratios.

Then, with respect to each of the selected peaks, the standard deviation of the absorbance ratios of the measurement samples S1 to S10 is calculated. The absorbance ratios and the calculated standard deviations of the selected peaks in the measurement samples S1 to S10 are shown in FIG. 7.

Thus, the standard deviations are calculated based not on the absorbances but on the absorbance ratios. Therefore, the evaluation results are hardly affected by a measurement error of a spectroscopic analyzer and can be highly accurately obtained.

Particularly, the benzene ring is structurally stable, and the peak of the benzene ring is clearly shown in the spectra in many cases. Therefore, when the absorbance ratios are calculated based on the absorbance of the peak at 1593 $cm^{-1}$ corresponding to the benzene ring, the dispersion degrees of the epoxy resins can be more accurately and readily evaluated.

Only the sampling operation is needed to spectroscopically analyze the measurement samples S1 to S10. It takes only several minutes to perform the sampling operation and the spectroscopic analysis. Therefore, as compared with the method using the TEM or the like, the method of this embodiment is capable of more readily evaluating the dispersion degrees of the epoxy resins in a shorter time. Furthermore, the sampling sites are distributed over a large area. Therefore, the area to be evaluated is not limited, and the dispersion degrees can be evaluated over the entire resin mixture.

The measurement samples S1 to S10 are spectroscopically analyzed by using the FT-IR. The spectroscopic analysis using the FT-IR is capable of obtaining more accurate results in a shorter time as compared with an analysis using a dispersion-type infrared spectroscopy or the like. Thus, by using the FT-IR, the dispersion degrees of the epoxy resins can be highly accurately evaluated in a short time.

As shown in FIG. 7, among the standard deviations of the selected peaks, the standard deviations of the peaks corresponding to the epoxy group and the p-disubstituted benzene are the maximum value of 0.021. The maximum standard deviation of 0.021 can be used as the threshold value for the epoxy resin dispersion degree evaluation.

Thus, a resin mixture having the same composition as the resin mixture 10 can be quantitatively evaluated with respect to the dispersion degrees of the epoxy resins by collecting samples from the resin mixture, calculating the standard deviations of the selected peaks, and comparing the maximum value of the standard deviations with the above threshold value (0.021).

When the maximum value of the calculated standard deviations is equal to or smaller than the threshold value, the resin mixture can be considered to have sufficient epoxy resin dispersion degrees and to improve the properties of the structural material containing the mixture. On the other hand, when the maximum value of the calculated standard deviations is larger than the threshold value, the resin mixture can be considered to have an insufficient epoxy resin dispersion degree.

Alternatively, an average value of the standard deviations of the selected peaks may be calculated to quantify the dispersion degrees of the epoxy resins. In this case, the dispersion degrees of the mixed epoxy resins can be represented by numerical values, and thereby can be quantitatively evaluated.

Figure 1:
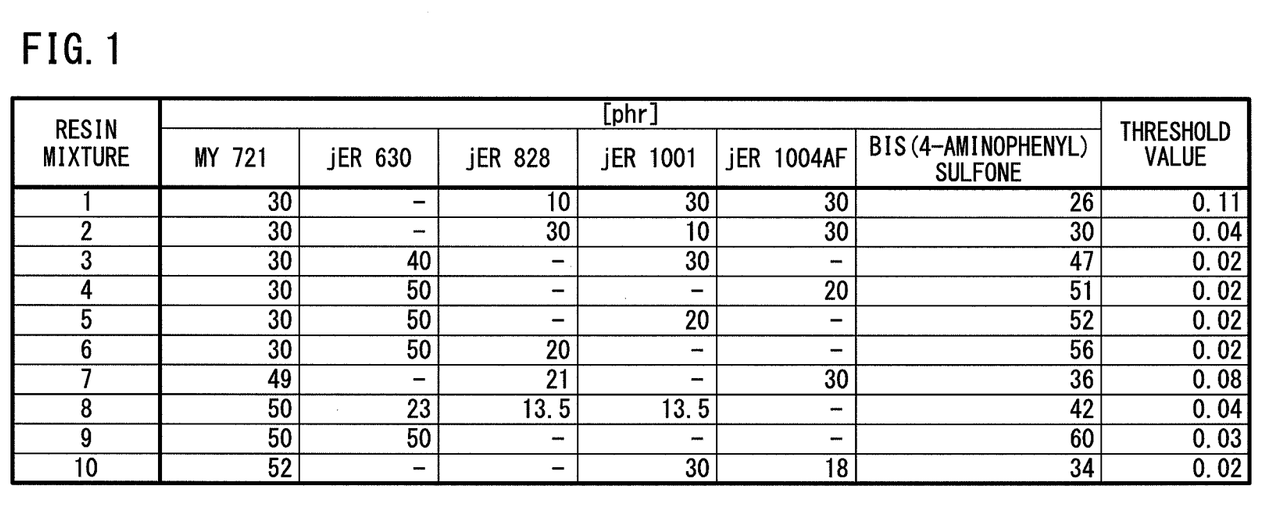
FIG. 1 is a table showing ratios of a plurality of aromatic epoxy resins and a hardener and a threshold value for dispersion degree evaluation in each resin mixture prepared in an embodiment of the present invention.

The standard deviations and the maximum values of the resin mixtures 1 to 9 shown in FIG. 1 can be obtained in the same manner. Resin mixtures having the same compositions as the resin mixtures 1 to 9 can be evaluated with respect to the dispersion degrees of the epoxy resins by using the maximum values as the evaluation standards (the threshold values). The composition ratios and the obtained threshold values of the resin mixtures 1 to 10 are shown in FIG. 1. As shown in FIG. 1, the threshold values are within a range of 0.01 to 0.11.

Of course, the resin mixtures having the same compositions as the resin mixtures 1 to 9 can be quantitatively evaluated with respect to the dispersion degrees of the epoxy resins in the resin mixtures by calculating the standard deviations of the selected peaks and by comparing the maximum values of the standard deviations with the threshold values shown in FIG. 1.

Whether the aromatic epoxy resins are sufficiently mixed or not (whether the aromatic epoxy resins are appropriately dispersed or not) can be judged by the evaluation method. When the kneading and the dispersion of the aromatic epoxy resins are judged to be insufficient, the kneading process may be continued. Then, after the elapse of a predetermined time from the judgment, the standard deviations and the maximum value may be obtained and compared with the threshold value again. On the other hand, when the kneading and the dispersion of the aromatic epoxy resins are judged to be sufficient, the kneading process may be stopped at the time.

In this embodiment, the kneading process can be continued until the dispersion degrees of the aromatic epoxy resins are judged to be sufficient in the resin mixture. Therefore, the properties of the structural material containing the resin mixture can be sufficiently improved, and the structural material can be prevented from having non-uniform properties. Thus, the physical and mechanical properties (such as the heat resistance and the mechanical strength) of the structural material can be prevented from being locally deteriorated.

Since the kneading process can be stopped when the dispersion degrees of the aromatic epoxy resins are judged to be sufficient, the mixing time can be controlled within an appropriate range. Thus, the kneading process is not continued for an excessively long time. Consequently, the resin mixture and the fiber-reinforced plastic can be efficiently produced, and the resin mixture can be prevented from being excessively hardened unexpectedly.

Also, the hardener is appropriately dispersed in the sufficiently mixed resin mixture. The resin mixture is uniformly mixed, whereby the hardening reaction uniformly proceeds, and the physical and mechanical properties can be prevented from being locally deteriorated. Thus, the structural material can have improved properties such as the heat resistance and the mechanical strength, and can be appropriately and efficiently hardened over the entire material.

In this embodiment, the standard deviations of the absorbance ratios are evaluated based on the different chemical structures and molecular weights of the mixed aromatic epoxy resins. Therefore, the dispersion degrees of the aromatic epoxy resins can be quantitatively evaluated regardless of the colors and the electron beam transmission properties of the resins.

As described above, the epoxy resin dispersion degree evaluation method of this embodiment is capable of readily and quantitatively evaluating the dispersion degrees of a plurality of aromatic epoxy resins in the resin mixture obtained by mixing the resins. Consequently, the method is capable of dispersing the epoxy resins in a minimal time under optimized mixing conditions and efficiently improving the properties of the structural material containing the resin mixture.

The present invention is not limited to the above embodiment, and various changes and modifications may be made therein without departing from the scope of the invention.

For example, the measurement samples S1 to S10 are taken from the ten sampling sites A1 to A5 and B1 to B5 in the above embodiment. The measurement samples are not particularly limited thereto as long as they are taken from a plurality of different sites in the resin mixture. It is preferred that the sampling sites of the resin mixture are distributed over a large area to improve the accuracy of the dispersion degree evaluation.

The eight functional group peaks are selected in the above embodiment. The peaks are not particularly limited thereto, and two or more common peaks of the measurement samples S1 to S10 may be selected.

The absorbance of the p-disubstituted benzene peak at 1593 cm$^{-1}$ is used as the standard absorbance in the above embodiment. However, the absorbance of another stable peak may be used as the standard absorbance.

The measurement samples S1 to S10 are spectroscopically analyzed by the attenuated total reflection (ATR) method using the FT-IR in the above embodiment. However, the spectra may be obtained by another spectroscopic analysis method such as a dispersion-type infrared spectroscopy.

The components of the resin mixture 10 shown in FIG. 1 were mixed at the same composition ratio. The total weight of the components was 300 to 600 g. 80 to 200 g of the hardener was added thereto, and the resultant was mixed at 150° C. in a 5-L kneading vessel 20. In the kneading process, a planetary blade was used at a kneading rate of 260 rpm.

Mixing times of 0, 1, 3, 5, 10 and 30 minutes were examined. Resin mixtures were prepared by mixing the above components for the mixing times, respectively, and were evaluated with respect to the dispersion degrees by the above method. The mixing time of 0 minute means that the components were not mixed.

A plurality of measurement samples were taken from the sampling sites A1 to A5 of FIG. 3 and the sampling sites B1 to B5 of FIG. 4 in each resin mixture at each mixing time. The measurement samples were spectroscopically analyzed by an ATR method using an FT-IR to obtain the spectra. In each spectrum, peaks P1 to P7 at 1610, 1504, 1288, 1103, 904, 826 and 548 cm$^{-1}$ were selected.

The absorbances of the selected peaks P1 to P7 were obtained from the peak heights, and were standardized based on the standard absorbance of the peak at 1593 cm$^{-1}$ to obtain the absorbance ratios. The standard deviations of the absorbance ratios of the selected peaks P1 to P7 were calculated, and the maximum value of the standard deviations was obtained.

Figure 8:
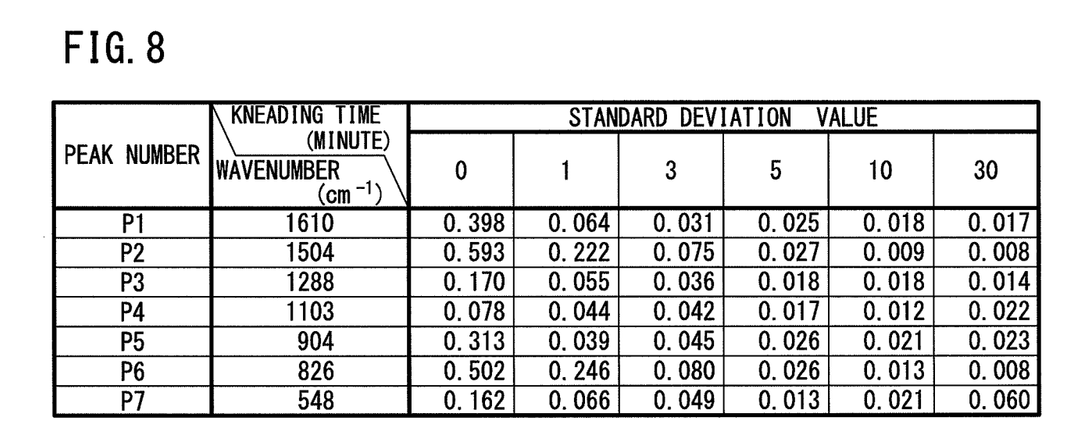
FIG. 8 is a table showing the relation between the standard deviations and the mixing times of the selected peaks.
Figure 9:
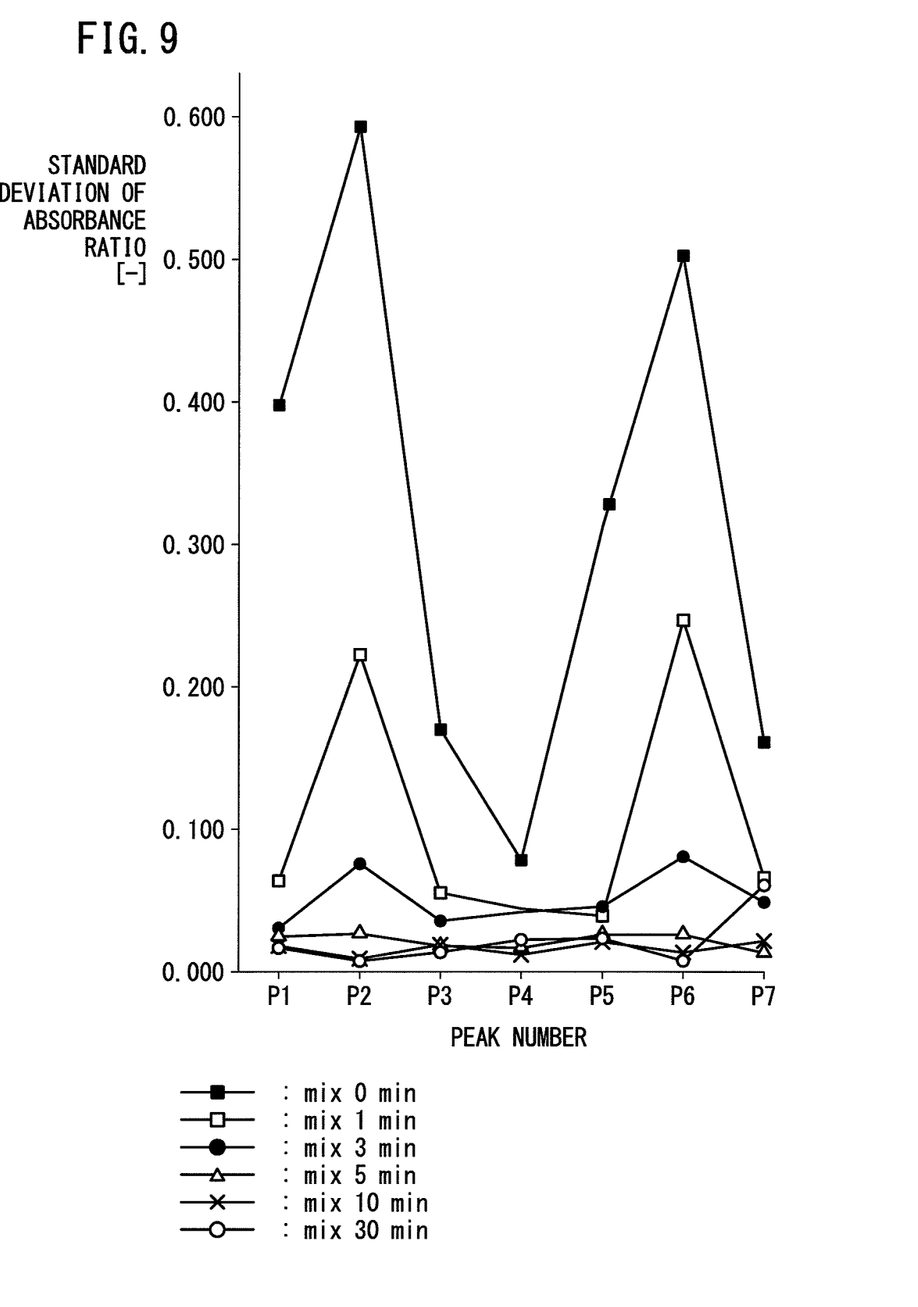
FIG. 9 is a graph showing the relation between the standard deviations and the mixing times of the selected peaks.

FIG. 8 is a table showing the wavenumbers of the selected peaks P1 to P7 and the maximum standard deviation values under the different mixing times. FIG. 9 is a graph showing the relation between the mixing times and the maximum standard deviation values of the selected peaks P1 to P7. In this graph, the numbers of the selected peaks P1 to P7 are on the horizontal axis, and the maximum standard deviation value is on the vertical axis.

As shown in FIGS. 8 and 9, in the resin mixtures prepared under the mixing time conditions of 0 to 3 minutes, the standard deviations of the selected peaks P1 to P7 are extremely different from each other. In the resin mixtures prepared under the mixing time conditions of 5 minutes or more, the differences between the standard deviations of selected peaks P1 to P7 become smaller than the threshold value of 0.02 shown in FIG. 1, and thus the epoxy resins are sufficiently dispersed in the resin mixtures.

Furthermore, in the resin mixtures prepared under the mixing time conditions of 10 minutes or more, the differences between the standard deviations of the selected peaks P1 to P7 are smaller than a certain value, and thus the epoxy resins are more appropriately dispersed. It is clear from the results that the aromatic epoxy resins can be satisfactorily dispersed in a mixing time of 5 minutes or more but at most 30 minutes in the above kneading process.

As described above, in the epoxy resin dispersion degree evaluation method of the present invention, the dispersion degrees of the mixed epoxy resins in the resin mixture can be readily and quantitatively evaluated by spectroscopically analyzing the resin mixture and by calculating the maximum standard deviation values of the selected peaks. Consequently, the epoxy resins can be dispersed in a minimal time under optimized mixing conditions, and the properties of the structural material containing the resin mixture can be efficiently and suitably improved.

What is claimed is:

1. A method of evaluating dispersion degrees of a plurality of aromatic epoxy resins in a resin mixture obtained by mixing the aromatic epoxy resins, the method comprising the steps of:
taking a plurality of measurement samples from a plurality of sites of the resin mixture,
spectroscopically analyzing the measurement samples to obtain spectra using a spectroscopic analyzer,
selecting a plurality of common functional group peaks in the spectra of the measurement samples,
standardizing absorbances of the selected peaks to obtain absorbance ratios, based on an absorbance of a standard peak, in each of the spectra obtained by the spectroscopic analyzer,
calculating standard deviations of the absorbance ratios of the selected peaks between the measurement samples, and
comparing a maximum value of the standard deviations with a predetermined threshold value to evaluate the dispersion degrees of the aromatic epoxy resins;
wherein the resin mixture contains at least two of a polyfunctional glycidylamine-type epoxy resin represented by a following structural formula (1), a p-aminophenol-type liquid epoxy resin represented by a following structural formula (2), and a bisphenol A-type liquid epoxy resin or a bisphenol A-type solid epoxy resin represented by a following structural formula (3):

(1)

(2)

(3)

wherein n is a number of repeating units in the structural formula (3).

2. The method according to claim 1, wherein the resin mixture is obtained by mixing 30 to 52 phr of the polyfunctional glycidylamine-type epoxy resin and 70 to 48 phr of at least one of the p-aminophenol-type liquid epoxy resin, the bisphenol A-type liquid epoxy resin, and the bisphenol A-type solid epoxy resin.

3. The method according to claim 2, wherein the resin mixture is obtained by mixing 30 to 52 phr of the polyfunctional glycidylamine-type epoxy resin, 23 to 50 phr of the p-aminophenol-type liquid epoxy resin, 10 to 30 phr of the bisphenol A-type liquid epoxy resin, and 10 to 30 phr of the bisphenol A-type solid epoxy resin.

4. The method according to claim 1, wherein the resin mixture contains 100 parts by weight of the aromatic epoxy resins and 26 to 60 parts by weight of a hardener.

5. The method according to claim 1, wherein the threshold value is 0.01 to 0.11.

6. The method according to claim 1, wherein the measurement samples are spectroscopically analyzed by a Fourier transform infrared spectroscopy, and the absorbances of the selected peaks are standardized to obtain the absorbance ratios based on an absorbance of a benzene ring at 1593 cm$^{-1}$.

7. The method according to claim 6, wherein peaks at 1610, 1504, 1288, 1103, 904, 826 and 548 cm$^{-1}$ are selected from the peaks in each of the spectra obtained by spectroscopically analyzing the measurement samples, and the absorbances of the selected peaks obtained respectively from heights of the selected peaks are standardized to obtain the absorbance ratios based on the absorbance of the benzene ring at 1593 cm$^{-1}$.

* * * * *